United States Patent [19]
Mann et al.

[11] Patent Number: 5,228,439
[45] Date of Patent: Jul. 20, 1993

[54] SYSTEM AND METHOD FOR MAINTAINING PROPER DEVICE OPERATION AT BATTERY DEPLETION BY SELF-REGULATING CURRENT DRAIN USAGE

[75] Inventors: Brian M. Mann, Beverly Hills; Leslie S. Miller, Saugus, both of Calif.

[73] Assignee: Siemens Pacesetter, Inc., Sylmar, Calif.

[21] Appl. No.: 844,258

[22] Filed: Mar. 2, 1992

Related U.S. Application Data

[63] Continuation-in-part of Ser. No. 691,928, Apr. 26, 1991, Pat. No. 5,127,402, which is a continuation of Ser. No. 448,191, Dec. 7, 1989, Pat. No. 5,031,616.

[51] Int. Cl.[5] .............................................. A61N 1/362
[52] U.S. Cl. ............................................... 128/419 PG
[58] Field of Search ................ 128/419 PG, 419 PS, 128/419 PT

[56] References Cited

U.S. PATENT DOCUMENTS

| | | | |
|---|---|---|---|
| 3,901,247 | 8/1975 | Walmsley | 128/419 PG |
| 4,120,306 | 10/1978 | Renirie | 128/419 PS |
| 4,120,307 | 10/1978 | Jirak et al. | 128/419 PT |
| 4,237,897 | 12/1980 | Beane et al. | 128/419 PG |
| 4,313,442 | 2/1982 | Knudson | 128/419 PG |
| 4,320,763 | 3/1982 | Money | 128/419 PG |
| 4,324,252 | 4/1982 | Rossing et al. | 128/419 PG |
| 4,390,020 | 6/1983 | Herpers | 128/419 PG |
| 4,590,941 | 5/1986 | Saulson et al. | 128/419 PG |
| 5,014,700 | 5/1991 | Alt | 128/419 PG |
| 5,031,616 | 7/1991 | Mann et al. | 128/419 PS |

Primary Examiner—William E. Kamm
Attorney, Agent, or Firm—Lisa P. Weinburg; Leslie S. Miller

[57] ABSTRACT

A system within an implantable stimulation device and a method for limiting the extent to which rate-responsiveness can be utilized during low battery periods. A battery threshold detector is utilized to detect when the battery is below a predetermined threshold. The implantable stimulation device then switches to base rate, but with a preset recovery time used to prevent rapid rate change. In an alternate embodiment, the device may then become rate-responsive again, but with a lower allowable maximum sensor rate being used.

26 Claims, 3 Drawing Sheets

SYSTEM AND METHOD FOR MAINTAINING PROPER DEVICE OPERATION AT BATTERY DEPLETION BY SELF-REGULATING CURRENT DRAIN USAGE

This application is a continuation-in-part of U.S. patent application Ser. No. 07/691,928 now U.S. Pat. No. 5,127,402, filed on Apr. 26, 1991, which is a continuation of U.S. patent application Ser. No. 07/448,191, filed on Dec. 7, 1989, the latter of which is now U.S. Pat. No. 5,031,616, which issued on Jul. 16, 1991.

BACKGROUND OF THE INVENTION

2. Field of the Invention

The present invention relates generally to implantable cardiac pacemakers, and more specifically to rate-responsive pacemakers wherein the upper rate is limited as the battery approaches its end-of-life (EOL).

Implantable cardiac pacemakers are powered by a battery within the pacemaker housing. Once implanted, it is difficult to determine the battery's state of depletion and, thus, the need for replacement. Although the surgery required for replacement is relatively minor, the associated risks of complications to the patient are ever present. In general, it is considered better to avoid replacement of a properly functioning pacemaker until absolutely necessary.

To determine when to explant a pacemaker prior to its EOL, physicians plan their follow-up schedules less frequently during the battery's "beginning-of-life" (BOL) and more frequently towards the battery's recommended replacement time (RRT) and the battery's "end-of-life" (EOL). (EOL is defined as the point in time in which the pacemaker pulse amplitude is reduced to approximately 50 percent of the programmed value.) As the basis, physicians estimate the remaining battery capacity by subtracting the "nominal" current drain of the pacemaker, usually specified at 5 volts with 100% pacing at a rate of 70 pulses-per-minute (ppm), from the theoretical available amp-hour capacity of the battery. Even though accurate battery capacity sensors have been developed (see, for example, U.S. Pat. No. 4,556,061 to Barreras et al.), the physician must still accurately predict the power consumption for the remaining period. With sophisticated pacemakers and unpredictable current drain modes of operation, physicians have to schedule more frequent follow-up visits to accurately monitor the replacement time and still avoid premature surgical replacement.

Current drain on a battery is largely dictated by the pacer output amplitude, pulse width, and rate. Programmability of these pacemaker parameters offers some flexibility to safely prolong the longevity of the battery. For example, it is well known that the battery life can be increased anywhere from 3 to 9 months by programming the rate to 70 instead of 90 beats-per-minute (BPM). However, not all patients can tolerate being paced at 70 BPM. Active patients need a higher rate during exercise. In patients with a normal sinus node, higher rates may be achieved with a dual chamber pacemaker, wherein the atrial rate is sensed and the ventricles are stimulated a short delay later (mimicking a normal heart). During exercise, the atrial rate may vary between 70 and 120 BPM or more.

It is also known that rate-responsive pacemakers can increase the pacing rate according to an additional sensor (such as an accelerometer or other "activity" sensor, oxygen saturation, QT measurements, respiration rate, temperature, etc.). The purpose of such pacemakers is to accelerate the rate when the atrium is incompetent, that is, nonresponsive to exercise stress or prone to atrial flutter or fibrillation.

In both of these pacemakers, the amount of current drain on the battery can change quite rapidly as the pacing rate of the pacer may change from a low rate to a high rate. This is especially true where the patient's own intrinsic rhythm is able to sustain the patient's needs at low activity levels (a low current drain condition), but where stimulated pacing is required in one or both chambers of the heart at a high activity level (a high current drain condition).

Unfortunately, such large variations in current drain can cause a sudden battery voltage drop below the EOL voltage level such that the possibility exists that the battery voltage could drop low enough to cause loss of capture. Furthermore, if pacing occurs at fast rates, such as occurs during exercise, the increase in current drain could dramatically reduce or even eliminate the safety margin associated with the last reported recommended replacement time (RRT) of the pacer, particularly when the last reported RRT is based on the current drain while the patient was at the rest rate.

It is also known in the art (see for example, U.S. Pat. No. 4,686,988 to Sholder) that battery current drain due to the delivered pacing pulse can be reduced by automatically adjusting the output amplitude and/or pulse width of the pacing pulse such that the lowest possible output is delivered which can still stimulate or "capture" the heart. This feature does ensure that the patient will not lose capture throughout the life of the pacemaker; however, this increase in processing time of the microprocessor and the constant changing of the output amplitude and/or pulse width introduces still more variables to consider when determining the replacement time of the pacemaker.

Furthermore, with the advent of microprocessor-based pacemakers, functionality has been extended to automatic adjustment of pacemaker parameters, storing and telemetering of intracardiac electrograms (EGMs), processing multiple sensors, detecting and breaking arrhythmias and recognizing waveform patterns. The current drain of the pacemaker may also be significantly influenced by the duty cycle of the microprocessor in performing these functions. Without careful monitoring of the battery voltage, these high current drain situations may cause a temporary drop in available battery voltage, increase the risk of loss of capture, and dramatically use up the remaining battery capacity.

A primary consideration is the avoidance at all costs of a situation in which a pacemaker suddenly and precipitously drops the pacing rate from a high rate during exercise to a base rate due to the battery voltage dropping relatively suddenly during high rate pacing. While this situation can have serious effects, a large number of pacemakers currently commercially available have just such a mode of operation. This also has the effect of greatly reducing the operational life of the pacemaker, since in active patients this may happen as long as years before the anticipated replacement time.

Eliminating this problem was the objective of the parent applications to the present specification. Accordingly, U.S. patent application Ser. No. 07/691,928 now U.S. Pat. No. 5,127,402, filed on Apr. 26, 1991, and U.S. patent application Ser. No. 07/448,191, filed on Dec. 7, 1989, the latter of which is now U.S. Pat. No. 5,031,616, which issued on Jul. 16, 1991, are both incorporated herein by reference.

In addition, in patients having dual chamber pacemakers in which the pacemaker is pacing in both the atrium and the ventricle, it can be deleterious to patient health to switch operation to ventricular pacing only when battery energy is limited toward EOL. Such pacemakers can expose the patient to "pacemaker syndrome," in which the patient may feel worse with the pacemaker pacing only the ventricle than the patient would feel with the pacemaker not pacing at all. In addition, in patients not having intact conduction, the loss of AV synchrony can seriously affect cardiac performance.

What is needed is a pacemaker which can regulate its own current drain usage, conserve the limited battery energy towards EOL, prevent loss of capture by limiting high current drain modes, and ultimately eliminate premature replacement of the pacemaker by eliminating the unpredictable nature of the RRT to EOL interval. Furthermore, this pacemaker should not burden the physician by increasing the number of follow-up visits near EOL.

SUMMARY OF THE INVENTION

The disadvantages and limitations of the background art discussed above are overcome by the present invention. The present invention may be used to limit power consumption as the battery approaches and exceeds the RRT. The present invention is capable of selectively altering operating parameters, based on a predetermined priority, to provide the longest possible active life for the pacemaker, while still providing a good quality of life as required by the patient's physiological needs. These actions help conserve the limited remaining battery energy and prevent loss of capture.

The present invention includes an implantable cardiac device having conventional components including a battery, a pulse generator for generating stimulating pulses, sense amplifiers for sensing cardiac signals, and a timing and control means. The device also includes a battery threshold detector for detecting a predetermined threshold level of the battery, and a processing means for switching to a lower current drain mode each time the battery threshold detector indicates that the battery voltage is below a prescribed threshold, but without suddenly and precipitously dropping the pacemaker rate. This configuration allows a significant reduction in current drain.

In the preferred embodiment, the implantable cardiac device is a rate-responsive pacemaker. Instead of immediately switching to a base rate of pacing, as is done in the prior art, the pacemaker will automatically and gradually decrease the pacing rate to a base rate over a period of time, in a manner analogous to the recovery time operation of a rate-responsive pacemaker. This is achieved by continuously monitoring the battery voltage for the occurrence of a voltage at or below the predetermined threshold during rate-responsive pacing.

If such a voltage is detected, the pacing rate is automatically and gradually reduced to a base rate according to a predefined schedule (which, in turn, quickly reduces the battery current drain). The base rate will remain in effect until the battery voltage is above the predetermined threshold or, optionally, until the pacemaker is otherwise reset. Optionally, if desired and as the battery continues to deplete, the allowable maximum sensor rate may be automatically reduced each time the battery voltage drops below the predetermined threshold.

In effect, the pacemaker is switching from a high current drain mode (rate-responsive pacing at a high rate), to a lower current drain mode (base rate pacing) until the battery voltage is above the predetermined threshold (optionally followed by rate-responsive pacing at a lower maximum rate). In other embodiments, the invention may also control the extent to which other high current drain modes can be utilized by the pacemaker once the predetermined threshold has been reached.

In the preferred embodiment, however, a dual chamber pacemaker always continues to pace both chambers of the heart to avoid pacemaker syndrome. In no case is a pacemaker constructed according to the teachings of the present invention allowed to suddenly and precipitously drop the pacing rate from a high rate to a low rate.

As such, the present invention does not require an increase in physician follow-up as the battery approaches RRT. Rather, its self-regulation of high current drain features allows the same follow-up schedule as VVI pacemakers with an increase in reliability and confidence.

Finally, all of the problems and disadvantages of the prior art are overcome in the present invention without incurring any substantial relative disadvantage. It will therefore be perceived that the advantages of the present invention result in extending the longevity of the pacemaker while providing a high quality of life for the patient for as long as possible, making the method of the present invention a highly desirable enhancement to implantable cardiac pacemaker therapy.

DESCRIPTION OF THE DRAWINGS

The features and other advantages of the present invention may be more readily understood by reference to the following description taken in conjunction with the accompanying drawings, in which.

DETAILED DESCRIPTION OF THE PREFERRED EMBODIMENT

Figure 1:
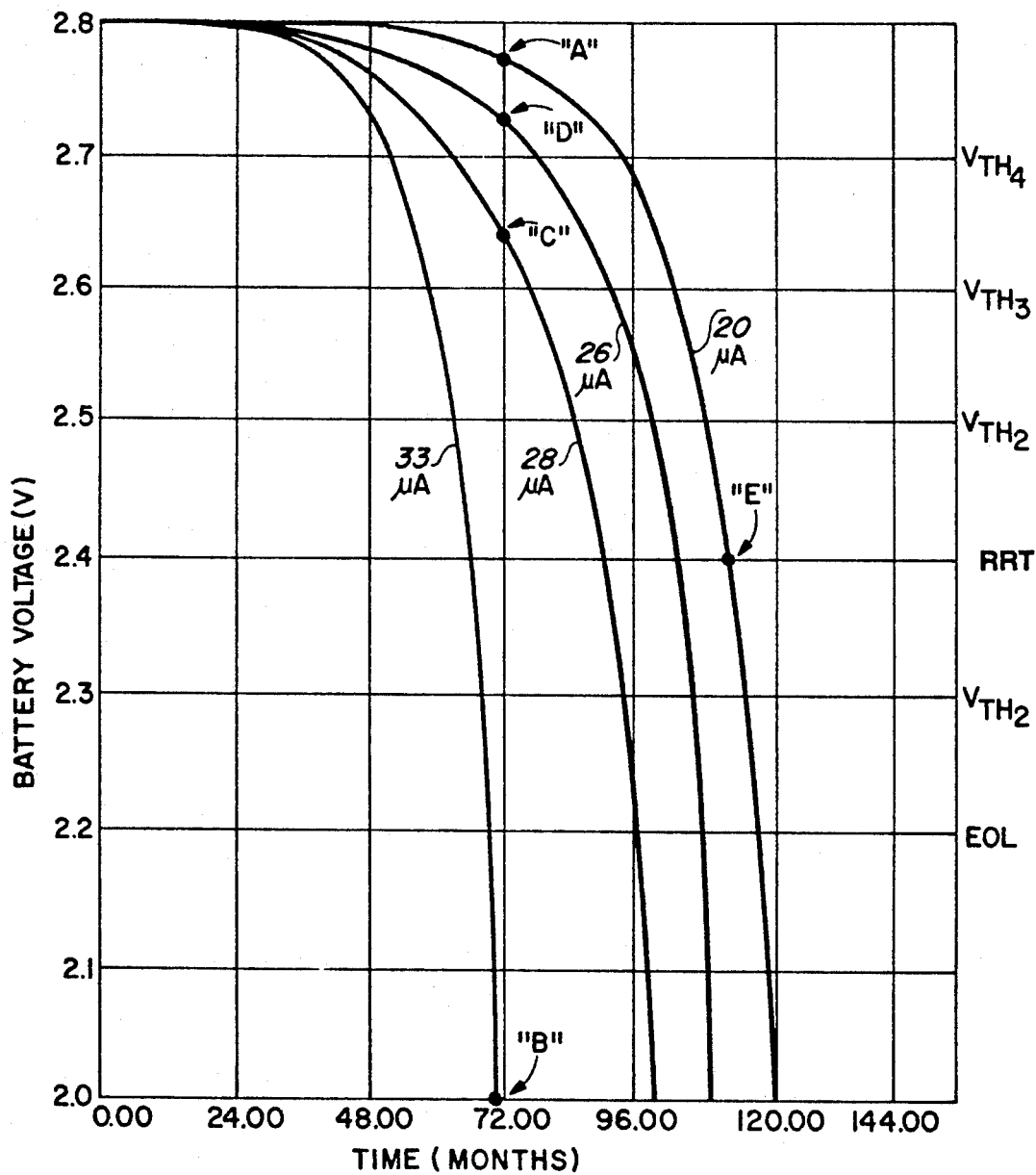
FIG. 1 shows plots of pacemaker battery voltage plotted versus time to illustrate the projected discharge characteristics of a typical lithium iodide battery at four different current drains.

The present invention may easily be understood with reference to FIG. 1 which shows the estimated discharge characteristics of a lithium iodide battery cell as is commonly used in many pacemakers today. These cells may be characterized as a fixed voltage source, with a stable open circuit voltage and an internal impedance which increases over time. Therefore, the available terminal voltage will vary inversely with the current drain from the battery, due to the internal voltage drop across the internal cell impedance.

As mentioned previously, the current drain is significantly influenced by the rate at which the pacemaker is delivering stimulating pulses. Point "A" in FIG. 1 represents a patient with a rate-responsive pacemaker wherein the patient is resting, therefore the current drain is low, say, at 20 uA. If the patient should suddenly need a high increase in rate, the current drain may increase to, say, 33 uA, and the available battery voltage would drop to 2.0 volts as indicated at point "B." It can therefore be seen that this increase in rate can cause a sudden battery voltage drop below the EOL voltage level such that the possibility exists that the battery voltage could drop low enough to cause loss of capture. By limiting the pacing rate such that the current drain was only 28 uA, the available battery voltage would rise to point "C," clearly well above the RRT threshold. A further reduction in the pacing rate, would enable the available battery voltage to rise to point "D" with an even greater safety margin.

It can further be easily seen in FIG. 1 that the remaining time to EOL is significantly increased as the operating point moves from point "B" to points "C," "D" and ultimately to "A." Once the battery terminal voltage reaches RRT at point "E," and the current drain cannot be reduced any further, the pacing rate is set to the Base Rate (or rest rate) and rate-responsive pacing is effectively suspended.

Figure 2:
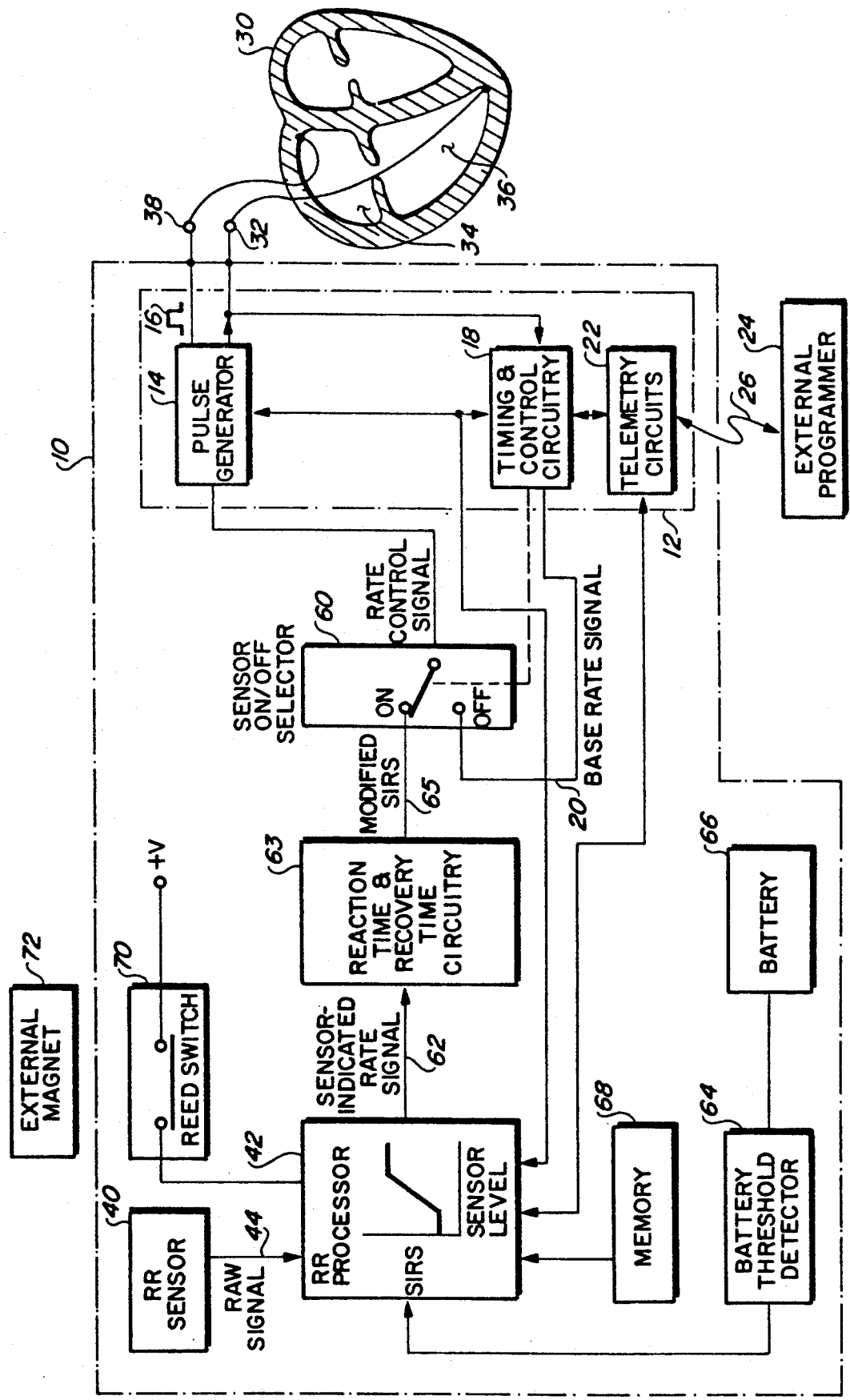
FIG. 2 is a block diagram of the present invention configured within a rate-responsive dual chamber pacemaker.

A block diagram of the present invention, coupled to a rate-responsive pacer, is shown in FIG. 2. A complete description of the rate-responsive pacemaker is included in U.S. Pat. No. 4,940,053, entitled "Energy Controlled Rate-Responsive Pacemaker Having Automatically Adjustable Control parameters," and U.S. Pat. No. 4,940,052, entitled "Microprocessor Controlled Rate-Responsive Pacemaker Having Automatic Rate Response Threshold Adjustment." These patents are assigned to the same assignee as is the present application, and these two patents are hereby incorporated herein by reference.

Briefly, the rate-responsive pacemaker functions as follows. A pacemaker 10 includes a conventional pacemaker chip 12, which has a pulse generator 14 for generating stimulating pulses 16 to a heart 30. Sense amplifiers (not shown) are employed to sense cardiac events and to communicate this information to timing and control circuitry 18. The timing and control circuitry 18 supplies a base rate signal 20 for the pulse generator 14, and controls the inhibition of a stimulus in the event of a sensed cardiac signal. Telemetry circuits 22 are connected electrically to the timing and control circuitry 18.

An external programmer 24 is used to noninvasively send programming signals to the telemetry circuits 22. These programming signals are depicted symbolically as the wavy line 26 in FIG. 2. It is noted that such signals are typically sent bi-directionally between the external programmer 24 and the pacemaker 10. In this way the external programmer 24 can noninvasively alter the pacemaker's programmable parameters.

A more complete description of the pacemaker chip 12, the external programmer 24, and their operation may be found in several patents. For example, note U.S. Pat. No. 4,232,679 to Schulman, entitled "Programmable Human Tissue Stimulator"; U.S. Pat. No. 4,686,988 to Sholder, entitled "Pacemaker System and Method for Measuring and Monitoring Cardiac Activity and for Determining and Maintaining Capture"; and U.S. Pat. No. 4,809,697 to Causey et al., entitled "Interactive Programming and Diagnostic System for Use with an Implantable Pacemaker." While not disclosing the exact same pacemaker chip 12 or circuits which are used in the preferred embodiment of the present invention, these patents nonetheless disclose the primary components of a conventional pacing system and teach the basic operation thereof. U.S. Pat. No. 4,232,679; U.S. Pat. No. 4,686,988; and U.S. Pat. No. 4,809,697 are hereby incorporated herein by reference.

The pulse generator 14 may be connected electrically to the patient's heart 30 via a lead 32. In the preferred embodiment, the pulse generator 14 is connected to the ventricle 36 and the atrium 34 via two leads 32 and 38, respectively. These leads 32 and 38 may be either unipolar leads, bipolar leads, or other multi-polar leads, all of which are known in the art.

The pacemaker 10 further includes at least one rate-responsive sensor 40 for sensing the physiological needs of the patient. In the preferred embodiment, the rate-responsive sensor 40 may be a piezoelectric sensor which detects physical activity. However, the present invention is not restricted to this type of sensor and could be used with any of the known rate-responsive sensors (QT, temperature, oxygen saturation, impedance, pre-ejection period (PEP), minute volume, accelerometers, etc.).

Since the invention described herein is independent of the type of sensor, hereinafter the sensor which is used to change the pacing rate shall simply be referred to as the "RR sensor." Furthermore, although the RR sensor 40 is shown in FIG. 2 as being included within the pacemaker 10, it is to be understood that the RR sensor 40 could also be included within, or coupled to, the leads 32 and 38, or otherwise placed external to the pacemaker 10.

In the preferred embodiment, the output of the RR sensor 40 is measured during each pacing cycle by the RR processor 42. Typically, the RR processor 42 includes means for converting the raw signal 44 to a sensor-indicated rate signal 62. In the preferred embodiment, the sensor-indicated rate signal 62 may be based on the average amplitude, which is an analog of the energy content of the raw signal 44.

The conversion may be accomplished in several ways, using conventional techniques: typically by a transfer curve, look-up table (stored or programmed into a memory 68), algorithmically, or in hardware, software or a combination thereof. Such a transfer curve is extensively discussed in the parent of the present application, which has been incorporated by reference above.

The sensor-indicated rate signal is supplied to reaction time and recovery time circuitry 63, which in turn supplies a modified sensor-indicated rate signal 65 to a switch 60. The reaction time and recovery time circuitry 63 limits the maximum positive and negative rates of change of the sensor-indicated rate signal, and thus limits the rate of change of the pacing rate. Reaction time is the minimum time required for an increase from the programmed base rate to the programmed maximum rate. Recovery time is the minimum time required for a decrease from the programmed maximum rate to the programmed base rate. Recovery time prevents the heart from slowing down too quickly.

In operation, the rate-responsive pacer may operate in either a SENSOR ON mode or a SENSOR OFF mode which can be selected by an appropriate programming signal received from the external programmer 24. The switch 60 is employed to select either the base rate signal 20 (during SENSOR OFF mode) determined by the timing and control circuitry 18 or the sensor-indicated rate signal 62 (during SENSOR ON mode) determined by the RR processor 42.

A battery threshold detector 64, connected to a battery 66, is used to detect a voltage above or below a predetermined threshold. In the preferred embodiment, the predetermined threshold is the result of an impedance level detected at RRT, however, other threshold levels may be contemplated without deviating from the basic teaching of the invention.

If the pacemaker 10 is pacing at an elevated rate due to exercise or stress and the battery 66 is at or below the RRT threshold level, then the battery threshold detector 64 triggers the RR processor 42 to decrease the sensor-indicated rate signal to the base pacing rate. The reaction time and recovery time circuitry 63 will operate to prevent the modified sensor-indicated rate signal from dropping quicker than allowed by the preset recovery time.

This reduction of pacing rate at RRT ensures that the remaining replacement time before EOL will not be rapidly used up, and that capture will be maintained.

In an alternative embodiment, an additional parameter may be used to select an RRT recovery time which may be different from the standard recovery time selected.

Figure 3:
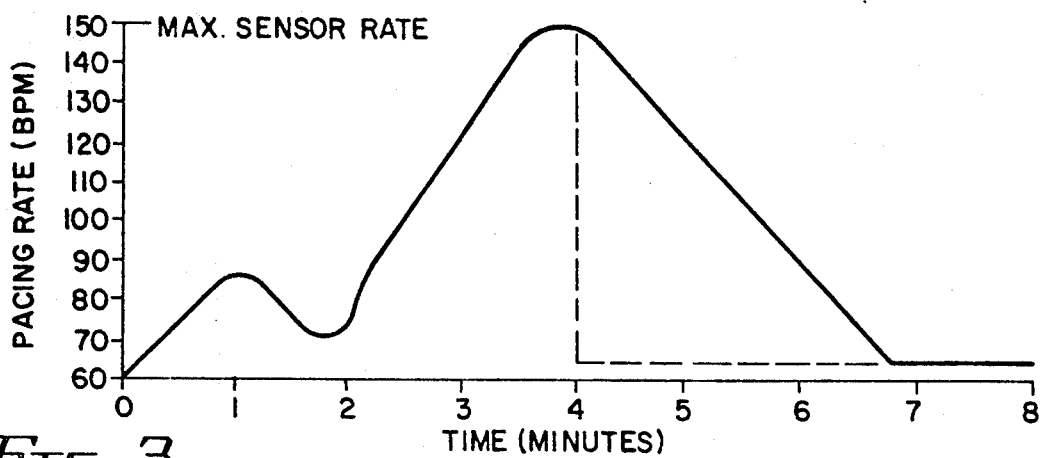
FIG. 3 is a plot of pacer rate versus time in a situation in which battery voltage is below a preset level, with the dotted line showing how previously known pacemaker designs implemented a sudden precipitous drop in pacer rate, and with the continuous line showing the operation of the present invention to drop the pacer rate over a period of time.
Figure 4:
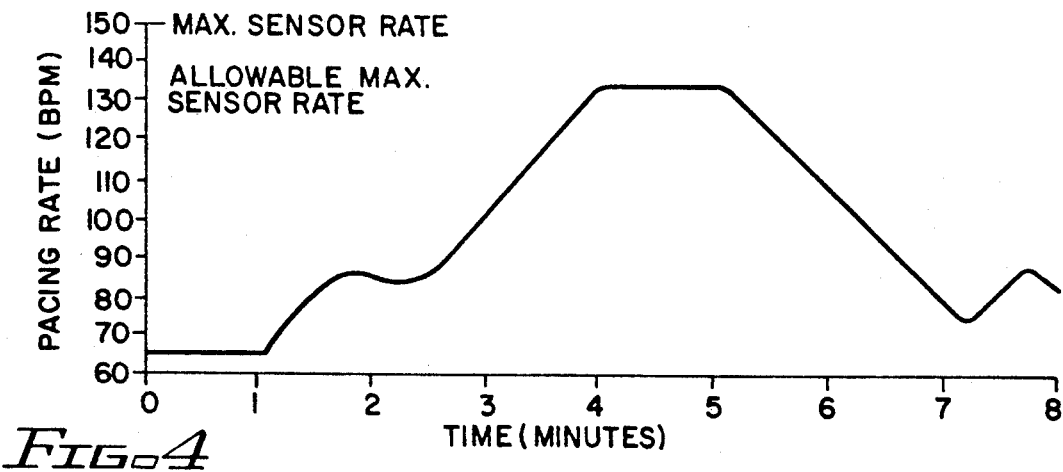
FIG. 4 is a plot of pacer rate versus time similar to that shown in FIG. 3, showing an alternate embodiment which allows a lowered maximum pacer rate after a period of time has elapsed from the drop illustrated in FIG. 3.

In FIG. 3, the operation of the prior art is illustrated by the dotted line. The pacemaker 10 is at maximum rate of 150 BPM just prior to the time of four minutes in FIG. 3. (Typically, in an active patient, the maximum sensor-indicated rate will be set as high as 150 BPM, and the minimum sensor rate may be set at 60 BPM or more.) At the four minute mark, the battery threshold detector 68 (FIG. 2) indicates that battery voltage has fallen (or the equivalent, that battery impedance has risen) to a critical point. At this four minute mark, the pacemaker of the prior art drops abruptly from 150 BPM to 65 BPM.

In the device of the present invention, the pacemaker 10 would drop to the same rate of 65 BPM, but at either the standard recovery time selected or, if different, at the RRT recovery time selected. Following this operation, in this first embodiment of the present invention, the rate would remain at 65 BPM. Note that this 65 BPM is a preset low pacing rate, which may be the same as, or more or less than, the minimum sensor rate. In this case, it is more than the minimum sensor rate.

In addition, in the preferred embodiment taught herein, a dual chamber pacemaker would continue to pace in both chambers. Alternately, dual chamber pacing could be momentarily interrupted if desired, and be resumed after a short time such as, for example, the standard recovery time selected or, if different, at the RRT recovery time selected.

A second embodiment of the present invention operates as described above with reference to FIG. 3, but instead of staying at 65 BPM will resume rate-responsive pacing after a time delay to allow battery voltage to stabilize at a higher value. This is illustrated in FIG. 3, where a lower allowable maximum sensor rate of 135 BPM replaces the former maximum sensor rate of 150 BPM. Instead of lowering the maximum sensor rate by 15 BPM, it may be lowered between 5 and 25 BPM or more.

Figure 5:
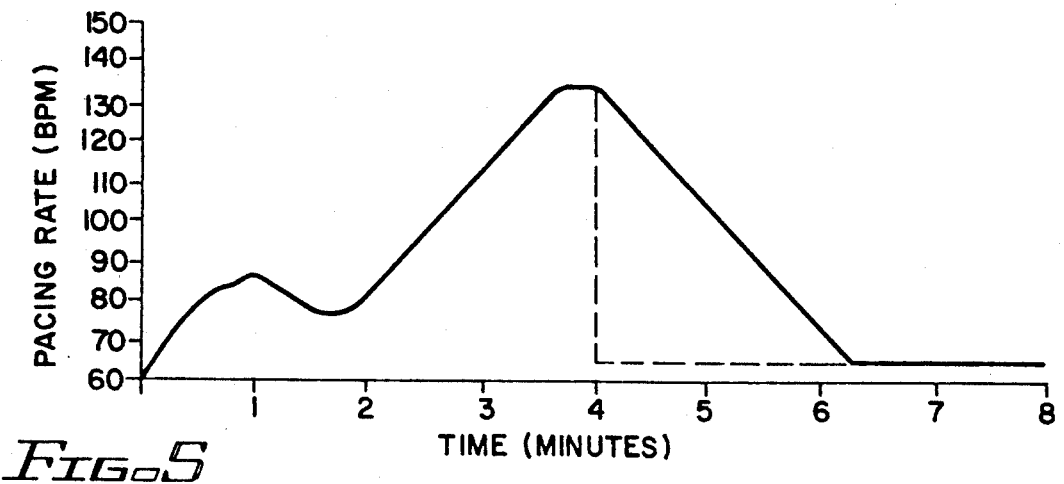
FIG. 5 is a plot of pacer rate versus time similar to those shown in FIGS. 3 and 4, in a situation in which battery voltage is again below the preset level as in FIG. 3, showing the operation of the present invention to again drop the lowered maximum pacer rate of FIG. 4 over a period of time.

Referring next to FIG. 5, after some time the battery will continue to decline as it ages, and even the allowable maximum sensor rate of 135 BPM will cause the operation described above with reference to FIG. 3 to occur again. At four minutes in FIG. 5, the sensor-indicated rate signal drops to 65 BPM, with the reaction time and recovery time circuitry 63 causing the pacing rate to drop to 65 BPM at either the standard recovery time selected or, if different, at the RRT recovery time selected. If desired, after a time a new allowable maximum sensor rate lower than 135 BPM may be set, with the pacemaker being rate-responsive, but at an ever-decreasing maximum rate.

It may therefore be appreciated by anyone skilled in the art that the invention can be extended to any pacemaker having a high current drain mode and successively lower current drain modes of operation. High current drain modes include rate-responsive pacing, automatic capture verification, automatic amplitude adjustment, automatic sensitivity adjustment, telemetry transmission of ECG data or measurements, waveform analysis, tachycardia or arrhythmia recognition, or any other features which increase microprocessor processing time. The pacemaker of the present invention would include a means for switching from a high current drain mode to a successively lower current drain mode whenever the battery threshold detector indicates that the battery voltage is below a prescribed threshold. Low current drain modes would be achieved by altering or limiting parameters such as reducing the sampling rate, pacing rate, or otherwise reducing the duty cycle of the microprocessor.

Furthermore, the present invention may incorporate a plurality of thresholds such that these high current drain features may be switched to lower current drain modes according to a predetermined priority based on basic life support and quality of life.

It may thus be appreciated from the above detailed description that the advantages of the present invention result in extending the longevity of the pacemaker while providing a higher quality of life for the patient for as long as possible, making the method of the present invention a highly desirable enhancement to implantable cardiac pacemaker therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An implantable pacemaker, comprising:

a battery having a battery voltage which is dependent on current drain from said battery;

a battery voltage threshold detector for detecting when said battery voltage drops below a first predetermined voltage level;

physiological sensing means for sensing a physiological parameter and generating a sensor-indicated rate signal as a function of the sensed physiological parameter, said sensor-indicated rate signal having as a maximum value a preset maximum sensor rate;

pulse generator means for generating stimulation pulses at a rate dependent on said sensor-indicated rate signal while said battery voltage is above said first predetermined voltage level;

energy conservation means for decreasing the pacing rate at which stimulation pulses are generated by said pulse generator means to a preset low pacing rate when said battery voltage threshold detector detects that said battery voltage is below said first predetermined voltage level; and means for limiting the rate at which said energy conservation means decreases the pacing rate to said preset low pacing rate.

2. An implantable pacemaker, as defined in claim 1, wherein said first predetermined battery level corresponds to a battery voltage characteristic of said battery at which replacement of the pacemaker is recommended.

3. An implantable pacemaker, as defined in claim 1, wherein said sensor-indicated rate signal has as a minimum value a preset minimum sensor rate.

4. An implantable pacemaker, as defined in claim 3, wherein said preset low pacing rate is equal to said preset minimum sensor rate.

5. An implantable pacemaker, as defined in claim 3, wherein said preset low pacing rate is greater than said preset minimum sensor rate.

6. An implantable pacemaker, as defined in claim 3, wherein said preset low pacing rate is less than said preset minimum sensor rate.

7. An implantable pacemaker, as defined in claim 1, wherein said pacemaker is a dual chamber pacemaker pacing both chambers of a heart, and wherein when said battery voltage threshold detector detects that said battery voltage is below said first predetermined voltage level, said pacemaker continues pacing both chambers of the heart.

8. An implantable pacemaker, as defined in claim 1, wherein said pacemaker is a dual chamber pacemaker pacing both chambers of a heart, and wherein when said battery voltage threshold detector detects that said battery voltage is below said first predetermined voltage level, said pacemaker temporarily paces only a single chamber of the heart, and after a short period resumes pacing both chambers of the heart.

9. An implantable pacemaker, as defined in claim 1, wherein said pacemaker is a dual chamber pacemaker pacing both chambers of a heart, and wherein when said battery voltage threshold detector detects that said battery voltage is below said first predetermined voltage level, said pacemaker temporarily paces only a single chamber of the heart, and when said battery voltage is no longer below said first predetermined voltage level resumes pacing both chambers of the heart.

10. An implantable pacemaker, as defined in claim 1, additionally comprising:

means for resetting said preset maximum sensor rate to a lower rate after said battery voltage threshold detector detects that said battery voltage is below said first predetermined voltage level; and means for disengaging said energy conservation means and resuming generating stimulation pulses at a rate dependent on said sensor-indicated rate signal so long as said battery voltage remains above said first predetermined voltage level.

11. An implantable pacemaker, as defined in claim 10, wherein said disengaging and resuming means operates a predetermined amount of time after the operation of said energy conservation means.

12. An implantable pacemaker, as defined in claim 10, wherein said disengaging and resuming means operates when said battery voltage is no longer below said first predetermined voltage level.

13. An implantable pacemaker, as defined in claim 10, wherein said energy conservation means, and said resetting means and disengaging and resuming means, are arranged and configured to operate repeatedly to lower the preset maximum sensor rate repeatedly.

14. An implantable pacemaker, as defined in claim 10, wherein said resetting means resets said preset maximum sensor rate to a rate which is between 5 and 25 BPM slower than it was before being reset.

15. An implantable pacemaker, as defined in claim 1, wherein said pacemaker has a programmable recovery time which limits the rate at which stimulation pulses generated by said pulse generator means can decrease when said battery voltage is not below said first predetermined voltage, and wherein said means for limiting the rate at which said energy conservation means decreases the pacing rate limits the rate of decrease using the programmable recovery time.

16. An implantable pacemaker, as defined in claim 1, wherein said pacemaker has a programmable recovery time which limits the rate at which stimulation pulses generated by said pulse generator means can decrease when said battery voltage is not below said first predetermined voltage, and wherein said means for limiting the rate at which said energy conservation means decreases the pacing rate limits the rate of decrease using a programmable RRT recovery time different from said programmable recovery time.

17. An implantable pacemaker, comprising:

a battery having a battery voltage which is dependent on current drain from said battery;

a battery voltage threshold detector for detecting when said battery voltage drops below a first predetermined voltage level;

physiological sensing means for sensing a physiological parameter and generating a sensor-indicated rate signal as a function of the sensed physiological parameter, said sensor-indicated rate signal having as a maximum value a preset maximum sensor rate, said sensor-indicated rate signal also having as a minimum value a preset minimum sensor rate;

pulse generator means for generating stimulation pulses at a rate dependent on said sensor-indicated rate signal while said battery voltage is above said first predetermined voltage level;

energy conservation means for decreasing the pacing rate at which stimulation pulses are generated by said pulse generator means to a preset low pacing rate when said battery voltage threshold detector detects that said battery voltage is below said first predetermined voltage level;

means for limiting the rate at which said energy conservation means decreases the pacing rate at which stimulation pulses are generated by said pulse generator means to said preset low pacing rate;

means for resetting said preset maximum sensor rate to a rate 5-25 BPM lower than said preset maximum sensor rate was prior to being reset following said battery voltage threshold detector detecting that said battery voltage is below said first predetermined voltage level; and means for disengaging said energy conservation means and resuming generating stimulation pulses at a rate dependent on said sensor-indicated rate signal so long as said battery voltage remains above said first predetermined voltage level.

18. An implantable pacemaker, comprising:
a battery having a battery voltage which is dependent on current drain from said battery;
means for detecting when said battery voltage drops below a first predetermined voltage level;
means for sensing a parameter characteristic of increased metabolic need and generating a sensor-indicated rate signal as a function of the sensed physiological parameter;
means for generating stimulation pulses at a pacing rate dependent on said sensor-indicated rate signal while said battery voltage is above said first predetermined voltage level;
means for decreasing, at a predetermined non-instantaneous rate, the pacing rate to a preset low pacing rate when said battery voltage is below said first predetermined voltage level.

19. A method of conserving power in an implantable pacemaker, comprising:
detecting when said battery voltage drops below a first predetermined voltage level;
sensing a physiological parameter and generating a sensor-indicated rate signal as a function of the sensed physiological parameter, said sensor-indicated rate signal having as a maximum value a preset maximum sensor rate;
generating stimulation pulses at a rate dependent on said sensor-indicated rate signal while said battery voltage is above said first predetermined voltage level;
decreasing the pacing rate at which stimulation pulses are generated to a preset low pacing rate when said battery voltage is below said first predetermined voltage level; and
limiting the rate at which the pacing rate is decreased to said preset low pacing rate.

20. A method, as defined in claim 19, additionally comprising:
resetting said preset maximum sensor rate to a lower rate after said battery voltage is no longer below said first predetermined voltage level; and
terminating said decreasing step and resuming generating stimulation pulses at a rate dependent on said sensor-indicated rate signal so long as said battery voltage remains above said first predetermined voltage level.

21. A method, as defined in claim 20, wherein said terminating and resuming step operates a predetermined amount of time after the operation of said energy conservation means.

22. A method, as defined in claim 20, wherein said terminating and resuming step operates when said battery voltage is no longer below said first predetermined voltage level.

23. A method, as defined in claim 20, wherein said decreasing step, and said resetting step and said terminating and resuming step, operate repeatedly to lower the preset maximum sensor rate repeatedly.

24. A method, as defined in claim 23, wherein said resetting step resets said preset maximum sensor rate to a rate which is between 5 and 25 BPM slower than it was before being reset.

25. A method, as defined in claim 19, wherein a programmable recovery time limits the rate at which stimulation pulses may be generated can decrease when said battery voltage is not below said first predetermined voltage, and wherein said limiting step limits the rate of decrease using the programmable recovery time.

26. A method, as defined in claim 19, wherein a programmable recovery time which limits the rate at which stimulation pulses may be generated can decrease when said battery voltage is not below said first predetermined voltage, and wherein said limiting step limits the rate of decrease using a programmable RRT recovery time different from said programmable recovery time.

* * * * *